United States Patent [19]

Nies

[11] Patent Number: 5,571,204
[45] Date of Patent: Nov. 5, 1996

[54] FEMORAL PROSTHESIS

[75] Inventor: Berthold Nies, Darmstadt, Germany

[73] Assignee: Merck Patent Gesellschaft mit beschrankter Haftung, Darmstadt, Germany

[21] Appl. No.: 501,923

[22] Filed: Jul. 13, 1995

[30] Foreign Application Priority Data

Jul. 14, 1994 [DE] Germany .......................... 44 24 883.0

[51] Int. Cl.$^6$ ...................................... A61F 2/36
[52] U.S. Cl. ............................................... 623/23
[58] Field of Search ........................................ 623/22, 23

[56] References Cited

U.S. PATENT DOCUMENTS

| | | | |
|---|---|---|---|
| 4,562,598 | 1/1986 | Kranz | 623/22 |
| 4,650,489 | 3/1987 | Thompson | 623/22 |
| 4,888,022 | 12/1989 | Huebsch | 623/23 |
| 4,888,024 | 12/1989 | Powlan | 623/23 |
| 4,892,550 | 6/1990 | Huebsch | 623/22 |
| 5,133,767 | 7/1992 | Frey et al. | 623/23 |
| 5,290,311 | 3/1994 | Baumann | 623/23 |
| 5,340,362 | 8/1994 | Carbone | 623/23 |
| 5,376,123 | 12/1994 | Klaue et al. | 623/23 |
| 5,425,768 | 6/1995 | Carpenter | 623/23 |

FOREIGN PATENT DOCUMENTS

| | | | |
|---|---|---|---|
| 328848 | 8/1989 | European Pat. Off. | 623/23 |
| 434604 | 6/1991 | European Pat. Off. | 623/23 |
| 4272753 | 9/1992 | Japan | 623/23 |
| 7439 | 4/1994 | WIPO | 623/23 |

*Primary Examiner*—Michael J. Milano
*Attorney, Agent, or Firm*—Millen, White, Zelano, & Branigan, P.C.

[57] ABSTRACT

A femoral prosthesis for implantation by cementation, has the stem with a longitudinal borehole extending proximally to distally for the transprosthetic application of the bone cement. The prosthesis stem is surrounded by an elastic sheath of a biocompatible polymeric material in such a way that, on application of the cement, the sheath is filled advancing distally to proximally and, when the space between stem and bone bed is completely filled, pressed flush against the bone bed.

11 Claims, 2 Drawing Sheets

FEMORAL PROSTHESIS

FIELD OF THE INVENTION

The invention relates to an endoprosthesis for hip joint replacement, more specifically the relevant prosthesis stem for implantation into the femur, called "femoral prosthesis" hereinafter for brevity.

BACKGROUND ART

As is known, two implantation techniques are available for insertion of femoral prostheses. On the one hand, femoral prostheses can be implanted in the appropriately prepared proximal region of the femur by the cementation technique. In this case, the prosthesis stem is positively anchored in the bone bed using bone cement. On the other hand, appropriately shaped femoral prostheses can be implanted by the cementless technique. In this case, the aim is frictional anchoring ("pressfit") of the prosthesis stem with the bone bed.

The present invention is directed at a femoral prosthesis which is intended for implantation by the cementation technique and provides considerable improvements for this in respect of surgical technique, implantation result and useful life of the prosthesis.

Despite the current high state of development in respect of optimization of prosthesis design, composition and processing characteristics of bone cement systems, surgical and cementation techniques, the implantation result is still influenced by many situational factors and, moreover, depends to a high degree on the skill of the operator. Considerable problem points in this connection are the centering and fixing of the prosthesis appropriate for the anatomy, and the choice of the cement characteristics appropriate for the situation.

When commercially available bone cements of high viscosity are used, the insertion, centring and fixing of the prosthesis in the prepared bone bed which is provided with a bed of cement can be performed more easily and reliably because the prosthesis is scarcely able to change position again until the curing process is complete. However, homogeneous and pore-free mixing of high-viscosity bone cements is difficult. Application, for example using a bone cement press or gun, requires a large force to be exerted. In addition, it is scarcely possible, because of the low flowability, to produce a completely continuous cement covering between bone bed and prosthesis surface. However, this is precisely what is absolutely necessary for firm and permanent bonding and thus a long and useful life of the prosthesis.

Low-viscosity bone cements which are likewise commercially available can be processed considerably more easily and reliably in this respect. However, the positioning and fixing of the prosthesis are difficult so that, as a rule, additional measures are necessary to stabilize the seating of the prosthesis.

Further developments in cementing with low-viscosity cement aim at initial insertion of the prosthesis into the bone bed and correct positioning therein using centring devices, and only then filling the remaining free space in the bone bed with cement. In this case, the bone cement can be applied using a cement gun and/or by suction in with the aid of vacuum. In a further embodiment of this cementation technique, the cementing takes place after the insertion and fixing of the prosthesis by transprosthetic application. Femoral prostheses suitable for this have a longitudinal borehole extending proximally to distally in the stem, through which the bone cement is injected in order then to fill the bone bed advancing distally to proximally. Reference may be made to EP 0 434 604 A1 for an example of this technique. However, this technique also has disadvantages which may affect the success of the operation and the useful life of the prosthesis. Thus, for example, it cannot be precluded that the prosthesis surface is contaminated with blood and discharge and/or irrigation fluid, or that bleeding takes place into the applied cement covering which is undergoing curing. This results in a considerable weakening of the prosthesis/cement covering/bone bed bonding, so that there may be premature loosening and breaking out of the implant.

SUMMARY OF THE INVENTION

It is the object of the invention to design a femoral prosthesis suitable for transprosthetic application in such a way that contamination of the prosthesis surface and applied cement covering with blood, wound discharge and irrigation fluid cannot take place.

This object is achieved according to the invention by surrounding the stem of the femoral prosthesis with an elastic sheath of a biocompatible polymeric material.

The invention accordingly relates to a femoral prosthesis for implantation by cementation, wherein the stem thereof has a longitudinal borehole extending proximally to distally for the transprosthetic application of the bone cement, and the prosthesis stem is surrounded by an elastic sheath of a biocompatible polymeric material in such a way that, on application of the cement, the sheath is filled advancing distally to proximally and, when the space between stem and bone bed is completely filled, pressed flush against the bone bed.

BRIEF DESCRIPTION OF THE DRAWINGS

The invention is explained in detail by way of example with the aid of the drawing hereinafter.

DETAILED DESCRIPTION

Figure 1A:
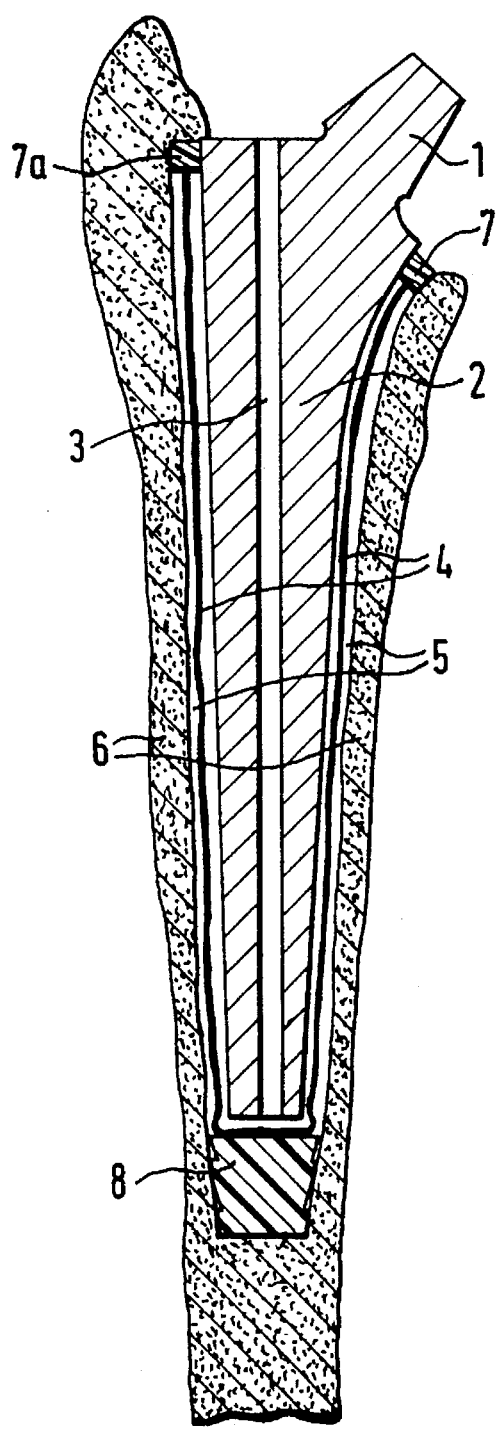
FIGS. 1(a), 1(b) and 1(c) show diagrammatically in a side view elevation process for the femoral prosthesis according to the invention in three consecutive phases (a), (b) and (c).
Figure 1B:
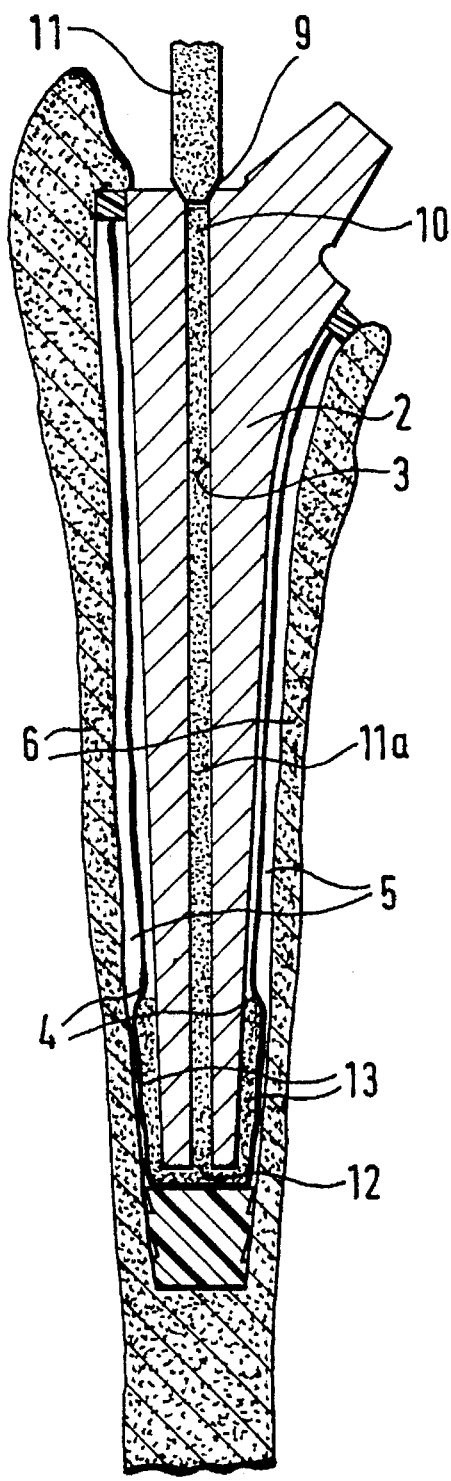
Figure 1C:
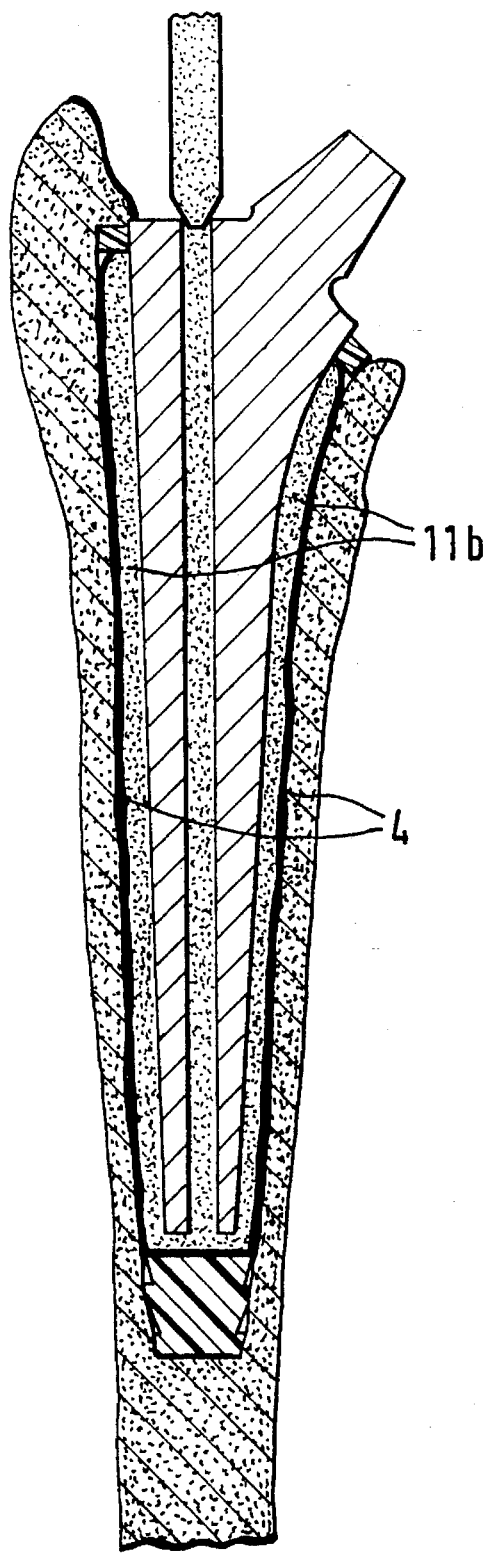

In phase (a), the femoral prosthesis 1 has already been inserted into the femur which has been appropriately prepared by removing the condyle and scraping out spongiosa. The stem 2 of the prosthesis has a longitudinal borehole 3 extending proximally to distally. The prosthesis stem 2 is surrounded by a sheath 4 which is essentially in close contact and is made of a biocompatible polymeric material. The remaining space 5 between stem 2 and inner surface of the bone bed 6 is provided for filling with bone cement. In the proximal region there are spacers 7, 7a for positioning and fixing the prosthesis. Below the distal end of the prosthesis stem, penetration of the bone cement to be applied into the medullary space is prevented by a medullary space blocker 8.

In phase (b), the outlet orifice 9 of a bone cement gun (not shown) is sited on the proximal orifice 10 of the longitudinal borehole 3 of the prosthesis stem 2. Bone cement 11, 11a has filled the longitudinal borehole 3 and emerges from the distal orifice 12 and starts to fill, advancing distally to proximally 13, the space 5 between stem 3 and bone bed 6, with the elastic sheath 4 being pressed flush against the bone bed 6.

In phase (c), the space 5 between the stem 3 and bone bed 6 is completely filled with bone cement 11b, and the sheath 4 is pressed over its whole area and flush against the bone bed 6.

The extent of the pressing can be controlled by the pressure applied to the cement. This pressure application both compacts the cement and further improves its mechanical properties, and strengthens the bonding between cement covering and prosthesis, especially with rough or surface-profiled prostheses.

It is particularly important the prosthesis/cement contact zone is protected from contamination throughout the implantation so that the bonding can be effected in an optimum manner.

The cementing process is complete when the cement filling has cured.

The invention can be modified advantageously by further embodiments.

Thus, for example, it is expedient to undertake the fastening of the sheath in the proximal region of the prosthesis stem by means of the spacers 7 which have been or are to be attached there. These spacers, which are used for centring, alignment and fixing the prosthesis in the proximal region, may be separate shaped articles. However, they may also be incorporated into the prosthesis itself as projections, beads or in the form of an encircling collar. Corresponding embodiments are known from the relevant state of the art.

It may furthermore be expedient to connect the sheath in the distal region to the medullary space blocker 8. In this case it is possible to insert the medullary space blocker and prosthesis into the femur in one step.

It is also possible for the medullary space blocker itself, where appropriate, to be provided with a centring device for the prosthesis or to be designed so that the distal end of the femoral prosthesis is fixed in position on insertion thereof by the medullary space blocker. Corresponding embodiments for medullary space blocker and, where appropriate, prosthesis stem tip are known from the relevant state of the art.

In a further embodiment, it is provided for the elastic sheath to have pores which widen on filling the sheath with bone cement so that the cement comes into contact with the bone bed. This has the advantage that a particularly intimate connection between the bone substance and the cement is formed at these points, so that the bone bed/cement/prosthesis bonding is further strengthened.

Suitable materials for the elastic sheath surrounding the prosthesis stem are in principle all biocompatible polymers as long as they are suitable for processing to sheets. These properties are fulfilled by most conventional synthetic polymers and a number of high molecular weight materials of natural origin. Synthetic materials which may be mentioned are alkene, fluoro, vinyl and acrylate polymers, and polyesters, polyamides and polyurethanes. Particularly preferred polymeric materials of natural origin are those which are bioabsorbable, that is to say are broken down by the body and, where appropriate, converted into endogenous substances. This applies to materials based on polylactides and polyglycolides and to biopolymers based on polypeptides or polysaccharides such as, for example, collagen, chitin and chitosan.

The preparation of polymeric materials of these types and the processing thereof to sheets and sheet products are known. For the present invention, these materials are expediently processed to sheet bubbles or stockings which are shaped so that they suit the particular prosthesis stem and can be pulled onto it in close contact.

The present invention has another advantage in that it is possible to modify the sheath material with additives which promote the healing process. Additives of this type can be, for example, osteoinductive and/or osteoconductive fillers. Examples thereof are calcium compounds such as calcium oxide, calcium carbonate and calcium phosphates, especially hydroxyapatite and tricalcium phosphate. These materials promote growth of bone and, in particular, the formation of mineralized bone matrix and thus favour the settling of the implant. It is furthermore advantageous to impregnate the sheath material with pharmaceutical agents such as, in particular, antibiotics and/or bone growth promoters. Examples thereof are antibiotics such as gentamicin and clindamycin and peptide growth factors such as, in particular, FGF and those of the BMP series.

The particular advantage thereof is that the agents can be specifically placed where they are needed and can display their effect appropriate for the purpose, namely in the region of contact with the bone bed. Compared with conventional implantation techniques using agent-loaded bone cements, in this case the optimal localization makes it possible to reduce the dose of agent.

It is possible in a particularly preferred embodiment for the invention to be designed in the form of an implantation kit. An implantation kit of this type consists of a femoral prosthesis for implantation by cementation, wherein the prosthesis stem has a longitudinal borehole extending proximally to distally for the transprosthetic application of the bone cement, of a sheath consisting of an elastic biocompatible polymeric material which is adapted in shape and dimension to the prosthesis stem and, where appropriate, in the pack unit a bone cement which is ready for use or is prepared for application.

In a further embodiment, a medullary space blocker with, where appropriate, centring device for the prosthesis can be attached at the distal end of the sheath in this implantation kit.

These embodiments provide, in a form suitable for practice, all the required components according to the invention needed by the operator to be able to carry out the implantation.

We claim:

1. A femoral prosthesis (1) for implantation by cementation in a bone bed (6), the prosthesis having a prosthesis stem (2) thereof with a longitudinal borehole (3) extending from a proximate end to a distal end for transprosthetic application of bone cement, the improvement comprising:

spaces (7) for centering and aligning the prosthesis in the proximal region;

a medullary space blocker (8) for fastening the sheath (4) in the distal region;

an elastic sheath (4) of a biocompatible polymeric material, the sheath (4) having pores therein and surrounding the prosthesis stem in such a way that, on application of the cement through the bore hole, the sheath is filled starting at the distal end and advancing to the proximate end of the prosthesis, wherein a space (5) between stem (2) and the bone bed (6) is completely filled, the elastic sheath (4) is pressed flush against the bone bed (6) and the pores widen so that the bone cement comes into contact with the bone bed (6).

2. The femoral prosthesis according to claim 1, wherein the sheath (4) is comprised of a bioabsorbable polymeric material.

3. The femoral prosthesis according to claim 2, wherein the sheath (4) is comprised of a bioabsorbable polymeric material containing osteoinductive and osteoconductive fillers.

4. The femoral prosthesis according to claim 3, wherein the sheath (4) is impregnated with agents which are selected from the group consisting of antibiotics and bone growth promoters.

5. A femoral prosthesis (1) for implantation by cementation in a bone bed (6), the prosthesis having the prosthesis stem (2) thereof with a longitudinal borehole (3) extending from a proximate end to a distal end for transprosthetic application of bone cement, the improvement comprising:

an elastic sheath (4) of a biocompatible polymeric material, the sheath (4) having pores therein and surrounding the prosthesis stem in such a way that, on application of the cement through the bore hole, the sheath is filled starting at the distal end and advancing to the proximate end of the prosthesis, wherein when a space (5) between stem (2) and the bone bed (6) is completely filled, the elastic sheath (4) is pressed flush against the bone bed (6) and the pores widen so that the bore cement comes into contact with the bone bed (6).

6. The femoral prosthesis according to claim 5, wherein the sheath (4) is fastened in the distal region to a medullary space blocker (8).

7. The femoral prosthesis according to claim 5, wherein the sheath (4) is comprised of a bioabsorbable polymeric material.

8. The femoral prosthesis according to claim 5, wherein the sheath (4) is comprised of a polymeric material selected of the group consisting of osteoinductive and osteoconductive fillers.

9. The femoral prosthesis according to claim 5, wherein the sheath (4) is impregnated with agents which are selected from the group consisting of antibiotics and bone growth promoters.

10. An implantation kit for implanting a prosthesis in a bone bed comprising:

(a) a bone cement which is ready for use and is prepared for application;

(b) a femoral prosthesis for implantation by cementation, wherein the prosthesis stem has a selected shape and a longitudinal borehole extending from a proximate end to a distal end for the transprosthetic application of the bone cement; and (c) a sheath comprising an elastic biocompatible polymeric material, which sheath is adapted in initial shape and dimensions to conform to the shape of the prosthesis stem, the sheath having pores which widen as the sheath is filed with bone cement introduced into the longitudinal bore hole of the prosthesis stem to expand the sheath outwardly to conform in shape and size to the inner surface of the bone bed.

11. The implantation kit according to claim 10, wherein medullary space blocker with, where appropriate, a centering device for the prosthesis is attached at the distal end of the sheath.

\* \* \* \* \*